United States Patent
Wessel et al.

(10) Patent No.: US 7,700,803 B2
(45) Date of Patent: Apr. 20, 2010

(54) CATALYSTS FOR PRODUCING CARBOXYLIC ACID SALTS

(75) Inventors: Helge Wessel, Mannheim (DE); Verena Seitz, Ludwigshafen (DE); Klaus Harth, Altleiningen (DE); Volker Bomm, Mutterstadt (DE); Nicola Christiane Aust, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 525 days.

(21) Appl. No.: 10/498,131

(22) PCT Filed: Dec. 6, 2002

(86) PCT No.: PCT/EP02/13842

§ 371 (c)(1),
(2), (4) Date: Jun. 9, 2004

(87) PCT Pub. No.: WO03/051513

PCT Pub. Date: Jun. 26, 2003

(65) Prior Publication Data
US 2005/0020850 A1 Jan. 27, 2005

(30) Foreign Application Priority Data
Dec. 14, 2001 (DE) ................ 101 61 674

(51) Int. Cl.
*C07C 51/00* (2006.01)

(52) U.S. Cl. .................................. 562/538

(58) Field of Classification Search ........... 562/539, 562/526, 538
See application file for complete search history.

(56) References Cited

U.S. PATENT DOCUMENTS

| | | | |
|---|---|---|---|
| 3,696,152 A | 10/1972 | Habermann et al. | |
| 4,250,111 A | 2/1981 | Seale et al. | |
| 4,782,183 A | 11/1988 | Goto et al. | |
| 5,292,936 A * | 3/1994 | Franczyk | 562/526 |
| 5,627,125 A * | 5/1997 | Ebner et al. | 502/331 |
| 6,646,160 B2 * | 11/2003 | Franczyk et al. | 562/539 |

FOREIGN PATENT DOCUMENTS

| WO | 94/24091 | 10/1994 |
|---|---|---|
| WO | 01/77054 | 10/2001 |

OTHER PUBLICATIONS

RD 354037, Oct. 1993.*
Kurr, Patrick et al., "Microstructural characterization of Cu/ZnO/A1203 catalysts for methanol steam reforming—A comparative study", Applied Catalysis A: General 348 (2008) pp. 153-164.
Gunter, M.M., et al., "Implication of the microstructure of binary Cu/ZnO catalysts for their catalytic activity in methanol synthesis", Catalysis Letters vol. 71, No. 1-2, 2001, pp. 37-44.
Fujitani, T. et al., "The effect of ZnO in methanol synthesis catalysts on Cu dispersion and the specific activity", Catalysis Letters 56 (1998) pp. 119-124.
Topsoe, Nan-Yu et al., "FTIR studies of dynamic surface structural changes in Cu-based methanol synthesis catalysts", Journal of Molecular Catalysis A: Chemical 141 (1999) pp. 95-105.
Gunter, M.M. et al., "Redox Behavior of Copper Oxide/Zinc Oxide Catalysts in the Steam Reforming of Methanol Studied by in Situ X-Ray Diffraction and Absorption Spectroscopy", Journal of Catalysis 203, (2001) pp. 133-149.

* cited by examiner

*Primary Examiner*—Taylor Victor Oh
(74) *Attorney, Agent, or Firm*—Novak Druce + Quigg LLP

(57) ABSTRACT

Catalysts for preparing carboxylic acid salts from alcohols which
a) consist of copper or
b) comprise from 99.9 to 10% by weight of copper and from 0.01 to 90% by weight of iron and from 0 to 50% by weight of one or more other metals,
and may optionally be doped, the hydroxides being obtained by precipitation of copper salt solutions or by coprecipitation of copper and iron salt solutions optionally containing salts of other metals using a base, and being reduced by hydrogen.

6 Claims, No Drawings

CATALYSTS FOR PRODUCING CARBOXYLIC ACID SALTS

The present invention relates to catalysts for preparing carboxylic acid salts based on copper.

WO-A1-94/24091 discloses catalysts for preparing aminocarboxylic acid salts by coprecipitating salts of copper and zirconium with salts of chromium, titanium, niobium, tantalum, vanadium, molybdenum, magnesium, tungsten, cobalt, nickel, bismuth, tin, antimony, lead and germanium.

However, these catalysts leave something to be desired.

It is an object of the present invention to provide improved catalysts for preparing carboxylic acid salts.

We have found that this object is achieved by novel and improved catalysts for preparing carboxylic acid salts from alcohols which a) consist of copper or b) comprise from 99.9 to 10% by weight of copper and from 0.01 to 90% by weight of iron and from 0 to 50% by weight of one or more other metals, and may optionally be doped, characterized by the hydroxides being obtained by precipitation of copper salt solutions or by coprecipitation of copper and iron salt solutions optionally containing salts of other metals using a base, and being reduced by hydrogen.

The catalysts according to the invention may be obtained as follows:

A copper salt solution may be precipitated or a mixture of a copper salt solution and an iron salt solution and optionally salt solutions of other metals may be coprecipitated, batchwise or continuously, with a base in the pH range of from 7 to 14 at temperatures of from 5 to 100° C., preferably from 15 to 90° C., more preferably from 20 to 85° C., and a pressure of from 0.1 to 5 bar, preferably atmospheric pressure, and the precipitation or coprecipitation product, generally the corresponding hydroxides, may be, for example, washed with water, dried at from 50 to 250° C., optionally calcined at from 300 to 700° C. and then reduced at from 150 to 300° C. in a hydrogen stream. However, the reduction may also take place before calcining and, if necessary, calcining may be repeated.

The copper or copper/iron catalysts may be doped after coprecipitation or after the subsequent drying or after calcining by impregnation, electroless deposition, electrochemical deposition, CVD (chemical vapor deposition) or sputtering, preferably impregnation or electroless deposition, more preferably impregnation. Useful elements for doping include those referred to as "other metals" which may be applied in the form of soluble salts or as the metals themselves. When salts are applied, subsequent calcining is generally used for fixing. The dopant quantity may vary within a wide range, but it is generally from 0.001 to 5% by weight, preferably from 0.005 to 3% by weight, more preferably from 0.01 to 2% by weight, in particular from 0.02 to 1% by weight.

Examples of useful bases include alkali metal hydroxides, alkaline earth metal hydroxides, alkali metal carbonates, alkaline earth metal carbonates, alkali metal hydrogencarbonates, alkaline earth metal hydrogencarbonates, ammonia, water-soluble amines or mixtures thereof. Useful alkali metal hydroxides include lithium hydroxide, sodium hydroxide, potassium hydroxide, rubidium hydroxide, and cesium hydroxide, preferably lithium hydroxide, sodium hydroxide, and potassium hydroxide, more preferably sodium hydroxide, and potassium hydroxide. Useful alkaline earth metal hydroxides include beryllium hydroxide, magnesium hydroxide, calcium hydroxide, strontium hydroxide, and barium hydroxide, preferably magnesium hydroxide and calcium hydroxide, more preferably calcium hydroxide. Useful alkali metal carbonates include lithium carbonate, sodium carbonate, potassium carbonate, rubidium carbonate, and cesium carbonate, preferably lithium carbonate, sodium carbonate, and potassium carbonate, more preferably sodium carbonate, and potassium carbonate. Useful alkaline earth metal carbonates include beryllium carbonate, magnesium carbonate, calcium carbonate, strontium carbonate, and barium carbonate, preferably magnesium carbonate and calcium carbonate, more preferably calcium carbonate. Useful alkali metal hydrogencarbonates include lithium hydrogencarbonate, sodium hydrogencarbonate, potassium hydrogencarbonate, rubidium hydrogencarbonate, and cesium hydrogencarbonate, preferably lithium hydrogencarbonate, sodium hydrogencarbonate, and potassium hydrogencarbonate, more preferably sodium hydrogencarbonate, and potassium hydrogencarbonate. Useful alkaline earth metal hydrogencarbonates include beryllium hydrogencarbonate, magnesium hydrogencarbonate, calcium hydrogencarbonate, strontium hydrogencarbonate, and barium hydrogencarbonate, preferably magnesium hydrogencarbonate and calcium hydrogencarbonate, more preferably calcium hydrogencarbonate. Examples of useful water-soluble amines include ammonia, methylamine, dimethylamine, trimethylamine, ethylamine, diethylamine and triethylamine, preferably ammonia, dimethylamine, trimethylamine and triethylamine, more preferably ammonia and trimethylamine.

Useful other metals include all metals of the groups IIa, IIIa, IVa, Va, VIa, IIb, IIIb, IVb, Vb, VIb, VIIb and VIII of the Periodic Table, such as beryllium, magnesium, calcium, strontium, barium, boron, gallium, indium, thallium, germanium, tin, lead, antimony, bismuth, selenium, tellurium, silver, gold, zinc, cadmium, scandium, yttrium, lanthanum, titanium, hafnium, vanadium, niobium, tantalum, chromium, molybdenum, tungsten, manganese, technetium, rhenium, cobalt, nickel, ruthenium, rhodium, palladium, osmium, iridium and platinum, and also cerium, preferably nickel, cobalt, chromium, zinc, lanthanum, ruthenium, rhodium, palladium, iridium and platinum, more preferably nickel, cobalt, zinc and lanthanum.

Useful salts of copper, iron and the other metals generally include all preferably water-soluble inorganic and organic salts.

Useful copper salts generally include all preferably water-soluble inorganic and organic salts, for example copper nitrate, copper chloride, copper sulfate, copper carbonate, copper hydrogencarbonate, copper hydrogensulfate, copper acetylacetonate and copper acetate, preferably copper nitrate, copper chloride, copper carbonate and copper acetate, more preferably copper nitrate, copper chloride and copper acetate.

Useful iron salts generally include all preferably water-soluble inorganic and organic salts, for example iron nitrate, iron chloride, iron sulfate, iron hexacyanoferrate, iron carbonate, iron hydrogencarbonate, iron hydrogensulfate, iron acetylacetonate and iron acetate, preferably iron nitrate, iron chloride and iron acetate, more preferably iron nitrate and iron chloride.

Useful salts of other metals generally include all preferably water-soluble inorganic and organic salts, for example nitrates, halides, sulfates, cyanides, hydroxides, carbonates, hydrogencarbonates, hydrogensulfates, acetylacetonates and acetates, preferably nitrates, halides, sulfates, carbonates, hydrogencarbonates and acetates, more preferably nitrates, halides, carbonates and acetates.

Depending on the origin of the starting material, the copper catalysts may contain impurities. In general, no purification is carried out.

The copper/iron catalysts comprise from 99.9 to 10% by weight, preferably from 95 to 20% by weight, more preferably from 90 to 30% by weight of copper, from 0.01 to 90% by weight, preferably from 3 to 75% by weight, more preferably from 5 to 60% by weight of iron and from 0 to 50% by weight, preferably from 0.1 to 35% by weight, more preferably from 0.5 to 25% by weight of one or more other metals, i.e. from one to eight, preferably from one to five, more preferably from one to three and in particular one or two other metals.

Greater preference is given to such catalysts which, as well as copper, comprise from 1 to 90% by weight of iron and are precipitated using NaOH at from pH 10 to 11.5 and a temperature of from 50 to 80° C., dried at from 180 to 220° C., calcined at from 450 to 550° C. and reduced using hydrogen at from 200 to 300° C. After reduction using hydrogen, these catalysts comprised a copper(II) oxide and/or copper(I) oxide content of from 0 to 35% by weight. A particular embodiment employs a catalyst having an aluminum content of less than 4% by weight, preferably from 3.99 to 0% by weight, more preferably from 3.99 to 1% by weight, in particular from 3.99 to 2% by weight. A further particular embodiment involves preparing the catalyst without zirconium.

Preference is given to preparing carboxylic acid salts from alcohols using such catalysts according to the invention which, before reduction using hydrogen, have a CuO crystal size of from 1 to 75 nm, more preferably from 2 to 50 nm.

The process for preparing carboxylic acid salts from alcohols according to the invention may be carried out as follows:

A pressure vessel, e.g. an autoclave, a tube reactor, a circulation reactor or a stirred tank battery may be charged in any desired sequence with alcohol, base, water and catalyst. The base is preferably dissolved in water before charging. Preference is given to initially charging the catalyst and then adding the alcohol separately from the aqueous base, or the alcohol together with the aqueous base. The closed pressure vessel is heated to a temperature of from 120 to 280° C., preferably from 140 to 240° C., more preferably from 150 to 220° C., resulting in an autogenous pressure which may be increased if required. The reaction takes place at a pressure in the range from the vapor pressure of the water to 75 bar, preferably from 2 to 50 bar, more preferably from 3 to 30 bar, in particular from 4 to 15 bar. In a particular embodiment of the production process, the reaction mixture comprises less than 4000 ppm, preferably from 3999 to 0 ppm, more preferably from 3999 to 1000 ppm, in particular from 3999 to 2000 ppm of aluminum ions.

Useful alcohols include ethylene glycol (derivatives) such as ethylene glycol oligomers or polymeric ethylene glycols and aminoalcohols such as ethanolamine, diethanolamine, triethanolamine, N,N-bis(2-hydroxyethyl)isopropylamine or tetrakis(hydroxyethyl)1,2-propylenediamine. Particularly useful alcohols have the general formula $$R-CH_2CH_2OH \qquad (I).$$

The radicals R, $R^1$ and $R^2$ in the alcohols of the general formula (I) are defined as follows:

R —$(OCH_2CH_2OH)$ or —$NR^1R^2$, preferably —$NR^1R^2$, $R^1$ and $R^2$ are each independently
  hydrogen,
  phenyl,
  —$CH_2CH_2OH$,
  $C_1$- to $C_{20}$-alkyl, preferably $C_1$- to $C_8$-alkyl, more preferably $C_1$- to $C_4$-alkyl such as methyl, ethyl, n-propyl, isopropyl, n-butyl, isobutyl, sec-butyl and tert-butyl, in particular methyl and ethyl,
  $C_2$- to $C_5$-dialkylamino such as dimethylamino, ethylmethylamino, diethylamino, ethyl-n-propylamino, ethyl-iso-propylamino, methyl-n-propylamino, methyl-iso-propylamino, methyl-n-butylamino, methyl-iso-butylamino, methyl-sec-butylamino and methyl-tert-butylamino, preferably dimethylamino, ethylmethylamino, diethylamino, ethyl-n-propylamino, ethyl-iso-propylamino, methyl-n-propylamino and methyl-iso-propylamino, more preferably dimethylamino, ethylmethylamino, diethylamino and ethyl-n-propylamino.

Aminocarboxylic acids and salts thereof (I) are useful intermediates for chelating agents, for example, in detergents, pharmaceuticals, agrochemicals such as pesticides, and also food and feed additives. Oxycarboxylic acids and salts thereof (I) prepared from ethylene glycol (derivatives) are useful intermediates for, for example, detergents.

EXAMPLES

Inventive Example 1

2.5 liters of an aqueous solution of 593 g of sodium carbonate were continuously introduced at 70° C. within 20 min with stirring into 2.5 liters of an aqueous solution of 1536.3 g of copper nitrate at pH 7 (with addition of $HNO_3$). After continued stirring at 70° C. for 30 minutes, filtering off, washing with a total of 100 liters of water and drying at 200° C. for 4 h, reduction was effected using hydrogen at 230° C. for 4 h.

The catalyst obtained had a copper content of 96.5% by weight and a cuprite content of 3.5% by weight. The CuO crystal size before reduction using hydrogen was 25 nm.

Inventive Example 2

4 liters of an aqueous solution of 948.8 g of sodium carbonate were continuously introduced at 70° C. within 35 min with stirring into 2.5 liters of an aqueous solution of 1536.3 g of copper nitrate at pH 9 (with addition of $HNO_3$). After continued stirring at 70° C. for 30 minutes, filtering off, washing with a total of 100 liters of water and drying at 200° C. for 4 h, reduction was effected using hydrogen at 230° C. for 4 h.

The catalyst obtained had a copper content of 97% by weight and a cuprite content of 3% by weight. The CuO crystal size before reduction using hydrogen was 28 nm.

Inventive Example 3

2 liters of an aqueous solution of 660 g of sodium hydroxide were continuously introduced at 70° C. within 20 min with stirring into 2.5 liters of an aqueous solution of 1536.3 g of copper nitrate at pH 11 (with addition of $HNO_3$). After continued stirring at 70° C. for 30 minutes, filtering off, washing with a total of 100 liters of water and drying at 200° C. for 4 h, reduction was effected using hydrogen at 230° C. for 4 h.

The catalyst obtained had a copper content of 92% by weight and a cuprite content of 8% by weight. The CuO crystal size before reduction using hydrogen was 21 nm.

Example 4

Non-Inventive

Inventive example 3 was repeated to produce a precipitated material which was filtered off and washed. The precipitated material was then dried at 150° C. for 4 h.

50 g of the dried precipitated material was impregnated according to its water takeup of 1.00 ml/g with 50 ml of an aqueous solution of 8.95 g of iron(III) nitrate hydrate within 1 h. Drying was then effected at 120° C. for 4 h, calcining at 500° C. for 2 h and reduction using hydrogen at 230° C. for 4 h.

The catalyst obtained had an iron content of 3% by weight. The CuO crystal size before reduction using hydrogen was 20 nm.

Inventive Example 5

2274 g of a 40% by weight aqueous solution of sodium hydroxide were continuously introduced at 70° C. with stirring into 2.5 liters of an aqueous solution of 1238.7 g of copper nitrate and 357.9 g of iron(III) nitrate nonahydrate within 20 min. After continued stirring at 70° C. for 30 minutes, filtering off, washing with a total of 100 liters of water and drying at 200° C. for 4 h, reduction was effected using hydrogen at 230° C. for 4 h.

The catalyst obtained had a copper content of 72% by weight. The CuO crystal size before reduction using hydrogen was 9 nm.

Inventive Example 6

Example 5 was repeated to produce a catalyst which had a copper content of 44% by weight by increasing the amount of iron salt used. The CuO crystal size before reduction using hydrogen was 10 nm.

Inventive Example 7

Example 5 was repeated to produce a catalyst which had a copper content of 10% by weight by increasing the amount of iron salt used. The CuO crystal size before reduction using hydrogen was 13 nm.

Comparative Example A

Example 19 of WO-A-94/24091 was repeated to produce a catalyst.

Hydrogenation Procedure

An autoclave having an internal volume of 300 ml was charged with 40 g of diethanolamine, 32 g of sodium hydroxide, 85 g of water and 4 g of the relevant catalyst. The reaction was carried on at a temperature of 170° C. and a constant pressure of 9 bar until hydrogen formation had ended. The amount of hydrogen released was recorded as a function of the reaction time. After the end of the reaction, the reaction product was analyzed. The results are summarized in the following table:

TABLE

| Catalyst | Reaction cycles | Reaction time [min] | Conversion [%] | Selectivity [%] |
| --- | --- | --- | --- | --- |
| Inventive example 3 | 1 | 164 | 99 | 98 |
| Example 4 | 1 | 176 | 99 | 98 |
| Inventive example 5 | 1 | 108 | 99 | 98 |
| Inventive example 6 | 1 | 84 | 99 | 99 |
| Comparative example A | 1 | 343 | 99 | 98 |
| Inventive example 3 | 10 | 212 | 99 | 95 |
| Example 4 | 10 | 288 | 98 | 96 |
| Inventive example 5 | 10 | 281 | 99 | 96 |
| Inventive example 6 | 10 | 252 | 98 | 96 |

We claim:

1. A process for preparing carboxylic acid salts, which comprises reacting alcohols of the group consisting of ethylene glycol oligomers and polymeric ethylene glycols and mixtures thereof with an alkali metal hydroxide, alkaline earth metal hydroxide or a mixture thereof in water
   in the presence of a copper catalyst which comprises from 99.9 to 10% by weight of copper and from 0.01 to 90% by weight of iron and from 0 to 50% by weight of one or more other metals,
   prepared by precipitation of copper salt solutions or by coprecipitation of copper and iron salt solutions optionally containing salts of other metals using a base, and reduction by hydrogen, at temperatures of from 120 to 280° C. and a pressure between the vapor pressure of the water and 75 bar, and said catalyst may optionally be doped after coprecipitation.

2. A process for preparing carboxylic acid salts as claimed in claim 1, wherein the content of aluminum ions in the reaction mixture is less than 4000 ppm.

3. A process for preparing carboxylic acid salts as claimed in claim 1, wherein the copper catalyst comprises from 5 to 60% by weight of iron.

4. A process for preparing carboxylic acid salts as claimed in claim 1, wherein the copper catalyst comprises from 5 to 90% by weight of iron.

5. A process for preparing carboxylic acid salts as claimed in claim 1 wherein said copper catalyst lacks a support.

6. A process for preparing carboxylic acid salts, which comprises reacting alcohols of the group consisting of ethylene glycol oligomers and polymeric ethylene glycols and mixtures thereof with an alkali metal hydroxide, alkaline earth metal hydroxide or a mixture thereof in water
   in the presence of a copper catalyst which consists essentially of from 99.9 to 10% by weight of copper and from 0.01 to 90% by weight of iron and from 0 to 50% by weight of one or more other metals,
   prepared by precipitation of copper salt solutions or by coprecipitation of copper and iron salt solutions optionally containing salts of other metals using a base, and reduction by hydrogen, at temperatures of from 120 to 280° C. and a pressure between the vapor pressure of the water and 75 bar, and said catalyst may optionally be doped after coprecipitation.

* * * * *